United States Patent
Karsak et al.

(10) Patent No.: US 8,800,939 B2
(45) Date of Patent: Aug. 12, 2014

(54) MOUNT TO ACCOMMODATE AN OBLONG MEDICAL INSTRUMENT

(75) Inventors: Oezcan Karsak, Herzogenaurach (DE); Norbert Scherer, Nuernberg (DE); Nikolaus Schoen, Hessdorf (DE)

(73) Assignee: Siemens Aktiengesellschaft, Munich (DE)

( * ) Notice: Subject to any disclaimer, the term of this patent is extended or adjusted under 35 U.S.C. 154(b) by 238 days.

(21) Appl. No.: 13/340,966

(22) Filed: Dec. 30, 2011

(65) Prior Publication Data
US 2012/0168587 A1 Jul. 5, 2012

(30) Foreign Application Priority Data
Dec. 30, 2010 (DE) .......... 10 2010 064 389

(51) Int. Cl.
*F16L 3/08* (2006.01)
*F16L 3/12* (2006.01)

(52) U.S. Cl.
USPC ............ 248/74.1; 606/53; 606/87; 606/151; 606/324

(58) Field of Classification Search
USPC ............ 600/429; 606/324, 151; 248/74.1, 65
See application file for complete search history.

(56) References Cited

U.S. PATENT DOCUMENTS

| | | | |
|---|---|---|---|
| 6,856,828 B2 * | 2/2005 | Cossette et al. | 600/429 |
| 7,043,961 B2 * | 5/2006 | Pandey et al. | 73/1.81 |
| 7,877,890 B2 * | 2/2011 | Weber | 33/613 |
| 7,993,353 B2 * | 8/2011 | Ro•ner et al. | 606/130 |
| 8,002,772 B2 * | 8/2011 | Sarin et al. | 606/53 |
| 8,535,329 B2 * | 9/2013 | Sarin et al. | 606/102 |
| 8,562,223 B2 * | 10/2013 | Hidano et al. | 384/463 |
| 2004/0039396 A1 * | 2/2004 | Couture et al. | 606/87 |
| 2005/0154296 A1 | 7/2005 | Lechner et al. | |
| 2008/0221625 A1 * | 9/2008 | Hufner et al. | 606/324 |
| 2009/0024127 A1 * | 1/2009 | Lechner et al. | 606/53 |
| 2009/0099445 A1 | 4/2009 | Burger | |
| 2009/0264940 A1 * | 10/2009 | Beale et al. | 606/86 R |
| 2009/0306499 A1 | 12/2009 | Van Vorhis et al. | |

FOREIGN PATENT DOCUMENTS

DE 10 2007 014 737 A1 9/2008

* cited by examiner

*Primary Examiner* — Amy J Sterling
(74) *Attorney, Agent, or Firm* — Schiff Hardin LLP

(57) ABSTRACT

A mount to accommodate an oblong medical instrument for computer-assisted surgery, has a clamp bracket with a variable cross section for clamped fixing of the instrument, and a localization device rotatable relative to the clamp bracket for detection of the spatial position of the instrument.

9 Claims, 5 Drawing Sheets

MOUNT TO ACCOMMODATE AN OBLONG MEDICAL INSTRUMENT

BACKGROUND OF THE INVENTION

1. Field of the Invention

The invention concerns a mount to accommodate an oblong medical instrument for computer-assisted surgery.

2. Description of the Prior Art

Surgical procedures are increasingly computer-assisted, thus implemented with simultaneous image monitoring. An operating instrument—a drill, a screwdriver or an awl, for example—is hereby positioned by the operating physician, and the operating instrument is rotated in order to effect the surgical procedure. As an alternative to manual implementation, it is also possible to position and rotate the instrument via a computer-assisted component such as a robot arm. For example, an x-ray image monitoring can be implemented in parallel with such instrument operation, within the scope of which images of the treatment region are continuously acquired and presented to the physician. In these images the physician can detect the instrument, which can be located automatically. Using the image exposures it is also possible to automatically determine the instrument tip shown in the image by suitable image analysis means, and to base the robot control on the determined spatial coordinates. However, in order to be able to use these operating instruments for computer-assisted surgery, they must be provided with a localization device that makes it possible to detect the instrument position with a localization system, so as to be able to determine the spatial position with respect to the spatial orientation of the instrument (and in particular its operating tip). By attaching a localization device to the instrument itself at a defined position relative to the tip and/or axis of the instrument, the localization of the tip/axis is possible. The use of optical localization systems in which, for example, appropriate optical markers are affixed to the instrument is known, as is the use of electromagnetic systems in which corresponding transmission and/or reception coils are arranged on the instrument.

However, it is problematic that the operating instruments of different manufacturers have different configurations, such that it is not possible to be able to attach an essentially standardized localization device to the instruments of different manufacturers. Moreover, the problem frequently exists that, during the rotation of the instrument as a result of the arrangement of the localization device on the instrument, the instrument is also moved, such that no position detection is possible at times since the localization system cannot detect the localization device at every rotation position of the operating instrument.

SUMMARY OF THE INVENTION

An object of the invention is to provide a mount that can fix different operating instruments while also allowing a localization to be possible at any time using a localization device.

To solve this problem, according to the invention a mount is provided to accommodate an oblong medical instrument for computer-assisted surgery, having a clamp bracket that is variable in terms of its retaining cross section for a clamped fixing of the instrument as well as a localization device that can be rotated relative to the clamp bracket for the detection of the spatial position of the instrument.

The mount according to the invention is suitable as a universal instrument adapter to accommodate different oblong operating instruments because the clamp bracket provided at the mounting side is adjustable (in terms of its retaining cross section) between a maximum clamping cross section and a minimum clamping cross section. This means that instruments that produce different strengths with respect to their different shapes in cross section can be fixed with the clamp bracket, consequently that different types of operating instruments can thus be fixed at the mount. It is primarily those instruments that have an instrument part that can be connected with the mount—which instrument part has a fixed axis of symmetry and ultimately transitions into an instrument tip—that can be used for fixing in the mount according to the invention. Among other things, screwdrivers, awls, drills, grinders and the like are examples of such instruments that can be engaged. The instrument part that is fixed at the clamp bracket can be, for example, cylindrical or prismatic or the like.

In addition to the clamp bracket that is variable in its retention cross section, the mount according to the invention also has a localization device provided at the mount, this localization device being rotatable relative to the clamp bracket. This means that the localization device is not arranged at the instrument itself but rather at the mount according to the invention, but the localization device is nevertheless firmly connected with the instrument. It is essential that the clamp bracket can be rotated relative to the localization device, meaning that the operating instrument—for example the drill—rotates during operation while the localization device is stationary. For this purpose, the localization device is supported at the mount by a corresponding rotation bearing so that the instrument can be rotated around its rotation axis relative to the localization device.

This arrangement allows the operating instrument to be stably located at any point in time and at any arbitrary rotation angle since the instrument movement does not affect the localization device, and no movement of the localization device results from the instrument movement, and consequently the localization device can be detected at any point in time by a corresponding localization system (a tracking camera or the like, for example). The instrument rotation consequently has no influence at all on the determination of the instrument position; visual contact or signal contact between localization system and localization device is presented at any point in time during the rotation. Since the localization device is also at rest during the procedure (since it does not rotate in any case), collision problems or the like are also precluded.

According to the invention, the clamp bracket is arranged on a support at which the localization device is supported such that it can rotate by a suitable rotation bearing. According to the invention, it is also provided that the localization device is rotatable around the center of the clamp bracket. Since the longitudinal axis of the oblong instrument is situated in the center of the clamp bracket, the localization device is consequently rotatable around the longitudinal axis of the instrument, i.e., the instrument is rotatable in the rotation axis of the localization device, such that any movement of the localization device given an instrument rotation is precluded. The rotation axis of the instrument and the rotation axis of the localization device coincide.

A roller bearing is preferably provided as the rotation bearing for the localization device, but the use of a slide bearing is also suitable. It is important that the bearing that is used enables a substantially friction-free rotation bearing. The roller or slide bearing can be arranged with a ring that is positionally fixed on the support while the localization device is arranged on an outer ring of the roller or slide bearing. The bearing can be a radial bearing whose inner ring is arranged on the support having the clamp bracket, and the localization device is arranged on its outer ring. The instrument consequently penetrates the roller or slide bearing and rotates therein.

According to a further embodiment, the clamp bracket itself has two clamp jaws that are movable relative to one another by means of at least one adjustment element, preferably so that a linear jaw motion is produced, for example by arrangement of the clamp jaws on linear guides (for example a swallowtail guide or the like) provided at the carrier. As an alternative, it is possible to support the clamp jaws such that they can pivot, as long as it is ensured that the instrument is always clamped with its longitudinal axis in the center of the rotation axis.

If two linear guides are provided, it is possible to provide only one adjustment element to move the clamp jaws, and therefore also to brace these jaws. As an alternative to the arrangement of the clamp jaws on corresponding linear guides, it is also possible to move both clamp jaws by means of two adjustment elements provided on the support, at which adjustment elements the clamp jaws are also linearly guided. For example, this means that two adjustment elements executed as bolts can be provided that can be rotated, but which are arranged so as to be fixed on the support and along which the clamp jaws can be moved and can simultaneously also be guided linearly.

In a further embodiment of the invention, such an adjustment element is preferably a bolt with two threaded segments rotating in opposite directions, one of which interacts with a clamp jaw. This embodiment of the bolts with two threaded segments rotating in opposite directions is advantageous because both clamp jaws can be moved toward or away from one another synchronously; both clamp jaws consequently always execute the same movement relative to the clamp center, such that the instrument to be clamped is always clamped with its longitudinal axis in the clamp center, and therefore in the rotation axis.

In a further embodiment of the invention the localization device has an arm supported so that it can rotate, with one or more localization elements (in particular optical markers or coils arranged on the arm) that can be detected by an external detection device (thus the localization system). This embodiment of the localization device with the arm (that is arranged or supported such that it can rotate on the bearing) enables the actual elements detected by the localization system—thus the optical markers or coils, at least one of which is provided—to be spaced somewhat relative to the mount so that the localization device is consequently also spaced sufficiently far from the procedure area.

DESCRIPTION OF THE PREFERRED EMBODIMENTS

Figure 1:
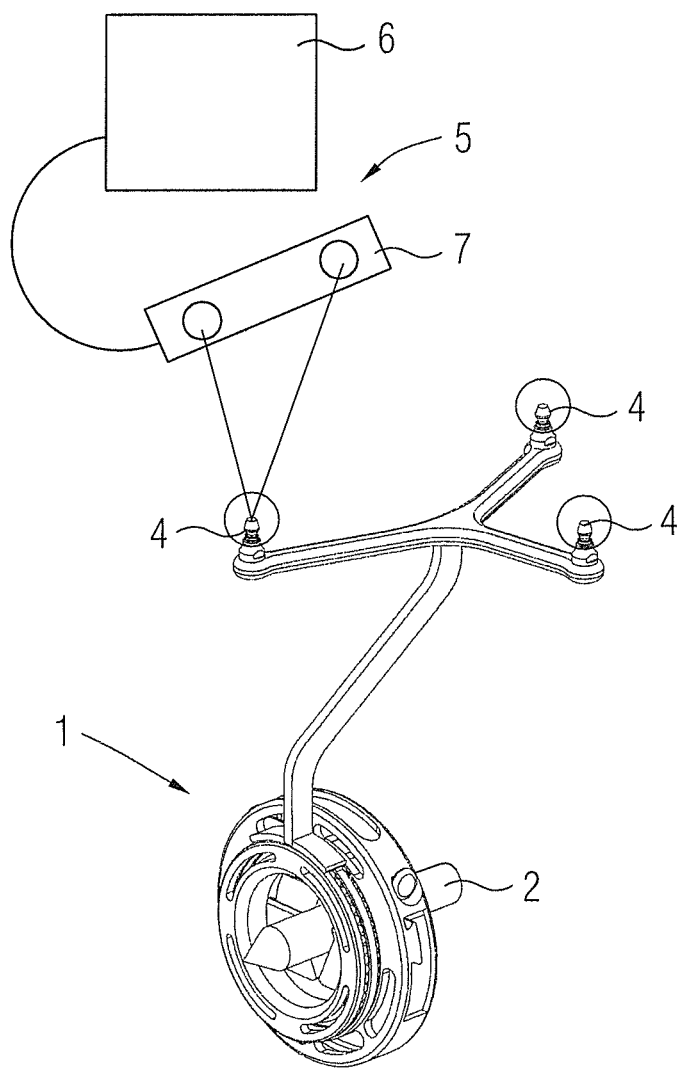
FIG. 1 is a schematic illustration of a mount according to the invention, in addition to an associated localization system.

FIG. 1 shows a mount 1 according to the invention at which an oblong medical instrument 2 (shown only in principle here) is arranged, for example a drill with which the operating physician can place a bore within the scope of a surgical procedure.

According to the invention, at the mount 1 a localization device 3 is provided at which three separate localization elements 4 (for example optical markers in the form of spheres or electromagnetic, signal-generating coils) are arranged in the shown exemplary embodiment. These localization elements 4 are detectable in terms of their spatial position by a localization system 6 that includes a suitable computer 6 as well as (for example) a stereo tracking camera 7, such that the concrete spatial position of the localization device 3 and—because the localization device 3 is correlated in terms of its position with the spatial position of the instrument 2—the spatial position or orientation of this instrument 2 can be detected from the registration data in the coordinate system of the localization system, and ultimately the position of the operating instrument tip can be determined.

Figure 2:
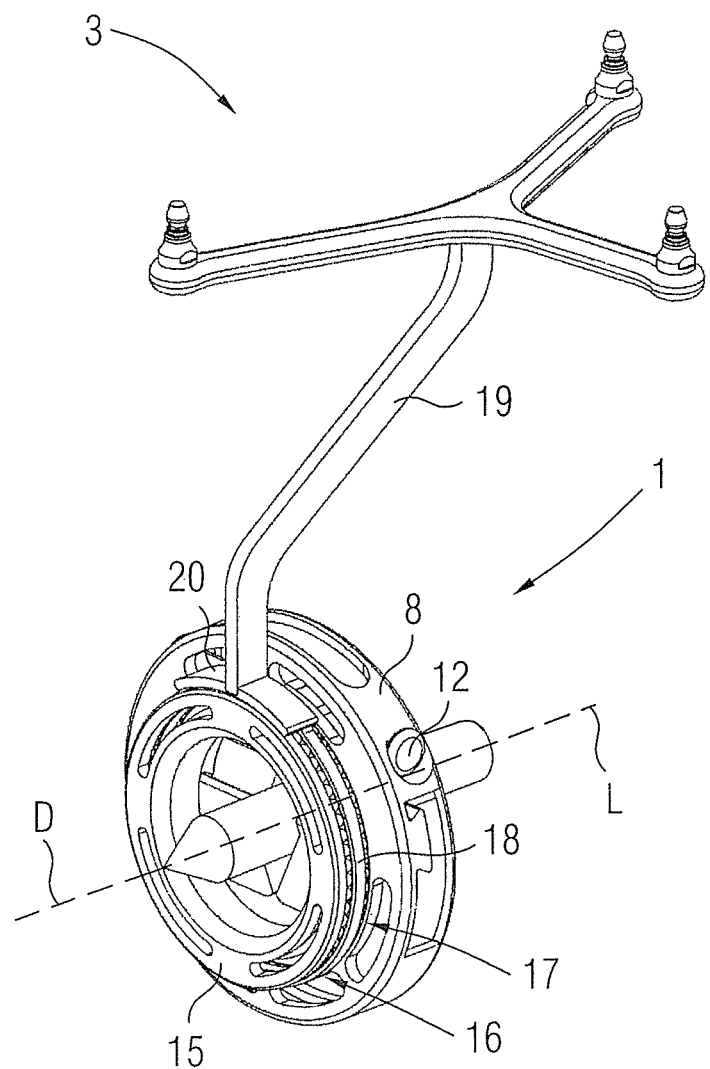
FIG. 2 is a perspective view of a first embodiment of the mount according to the invention.
Figure 3:
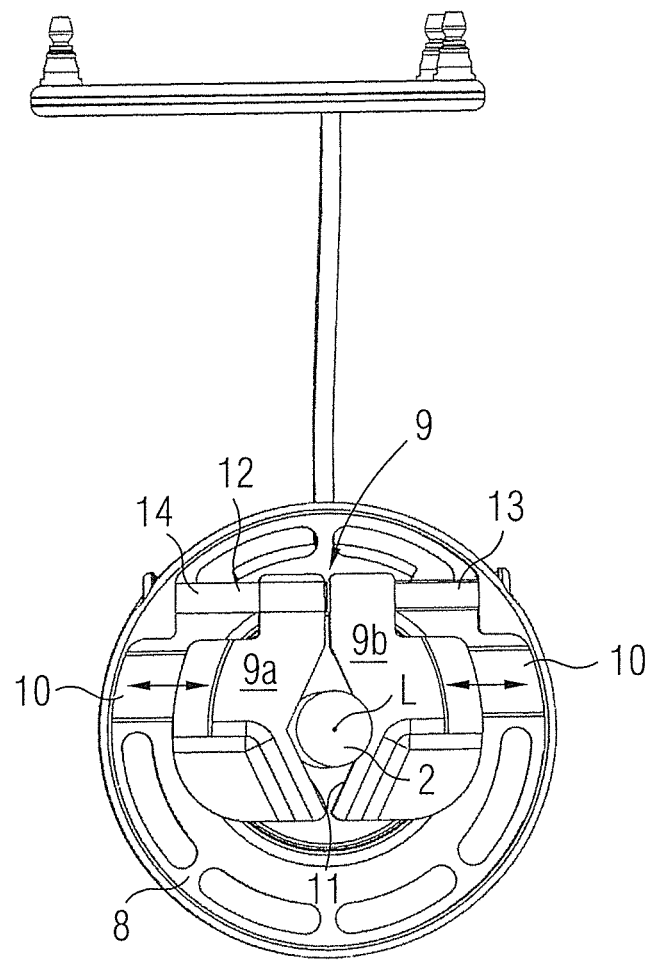
FIG. 3 is a rear view of the mount of FIG. 2.

Such a mount 1 that—as a universal instrument adapter—has the possibility to be able to hold instruments of different diameters or, respectively, cross section configurations is shown in an enlarged detail view in FIGS. 2 and 3. The mount 1 has a support 8 at which (see FIG. 3) a clamp bracket 9 with two clamp jaws 9a, 9b is arranged, the clamp jaws 9a, 9b being linearly displaceable on a linear guide 10 (here a swallowtail guide, for example), as indicated by the two double arrows. This means that the two clamp jaws 9a, 9b can be moved toward and away from one another.

The two clamp jaws 9a, 9b have two clamp surfaces or clamp segments 11 directed toward one another that, in the shown example, are respectively realized as two inclined surfaces 11. These clamp surfaces 11 laterally engage the instrument 2 and clamp it. The clamp surfaces 11 are executed and positioned so that the instrument to be clamped can be clamped with its central longitudinal axis L exactly in the rotation axis D of a rotation bearing (which is described further in the following). This means that, independently of the instrument cross section, the instrument 2 is always clamped via the clamp jaws 9a, 9b so that the respective longitudinal axis L of the instrument coincides with the rotation axis D. The minimum clamp diameter is limited by the design of the clamp jaws 9a, 9b; the maximum diameter is defined by the maximum clearance of the clamp jaws 9a, 9b, which is defined by the linear guide 10.

The adjustment element 12 (which here is executed as a bolt with two threaded segments 13, 14 rotating opposite one another) to be operated for linear displacement of the clamp jaws 9a, 9b also serves to secure the central clamping of the instrument 2. In FIG. 3, the bolt—which can be rotated manually or by machine—engages with the right threaded segment 13 at the right clamp jaw 9a, while the left threaded segment 14 engages at the left clamp jaw 9b. If the bolt is turned, the clamp jaws 9a, 9b are moved away from one another or towards one another (depending on the direction of rotation), simultaneously and with similar motion. This means that, by the use of a double-start bolt 12, it is ensured that the two clamp jaws 9a, 9b move simultaneously relative to the middle or the center of the clamp, namely the center between the two clamp jaws 9a, 9b. This center is situated the longitudinal axis L of the instrument 2 to be clamped. The use of an adjustment element in the form of a bolt 12 here is sufficient since the clamp jaws 9a, 9b are directed so as to be linearly movable at the two linear guides 10.

At the support 8, a rotation bearing 16—here in the form of a roller bearing 17—is also arranged on an axially protruding ring projection 15. This roller bearing 17 is arranged with its inner ring fixed on the annular projection 15; fixed on its outer ring is the localization device 3 with an attachment segment 20 arranged on an arm 19 of the localization device. As a result of the fixed connection of the inner ring with the ring projection 15, and therefore with the support 8 (and therefore with the clamp jaws 9a, 9b), the entire support 8 (in addition to the instrument 2 that is manually rotated by the physician, for example) can be rotated relative to the localization device 3 (which is held on the arm 19 by the physician, for example). No rotationally dependent movements of localization device 3 whatsoever occur relative to the rotating instrument 2 because—as noted—the rotation axis D of the rotation bearing 16 (thus of the roller bearing 17) coincides with the longitudinal axis L of the instrument 2; the instrument 3 consequently rotates in the center of the roller bearing 17.

Figure 4:
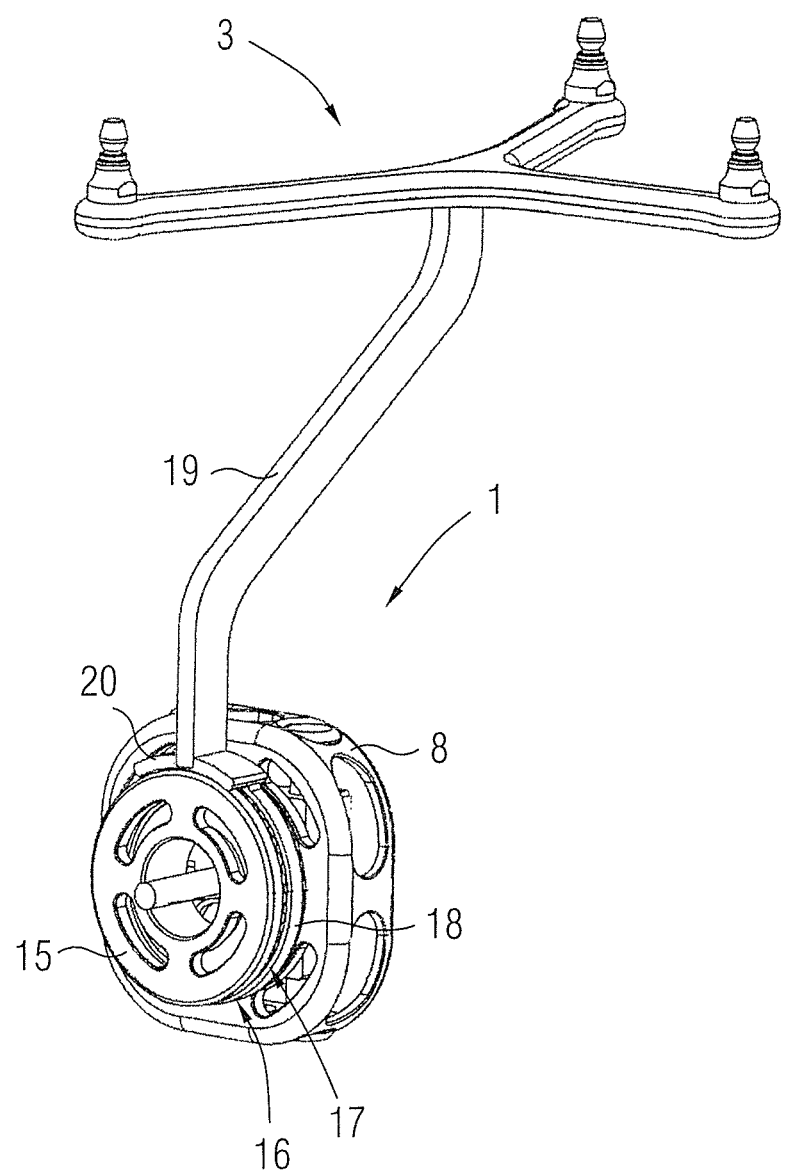
FIG. 4 is a perspective view of a mount of a second embodiment according to the invention.
Figure 5:
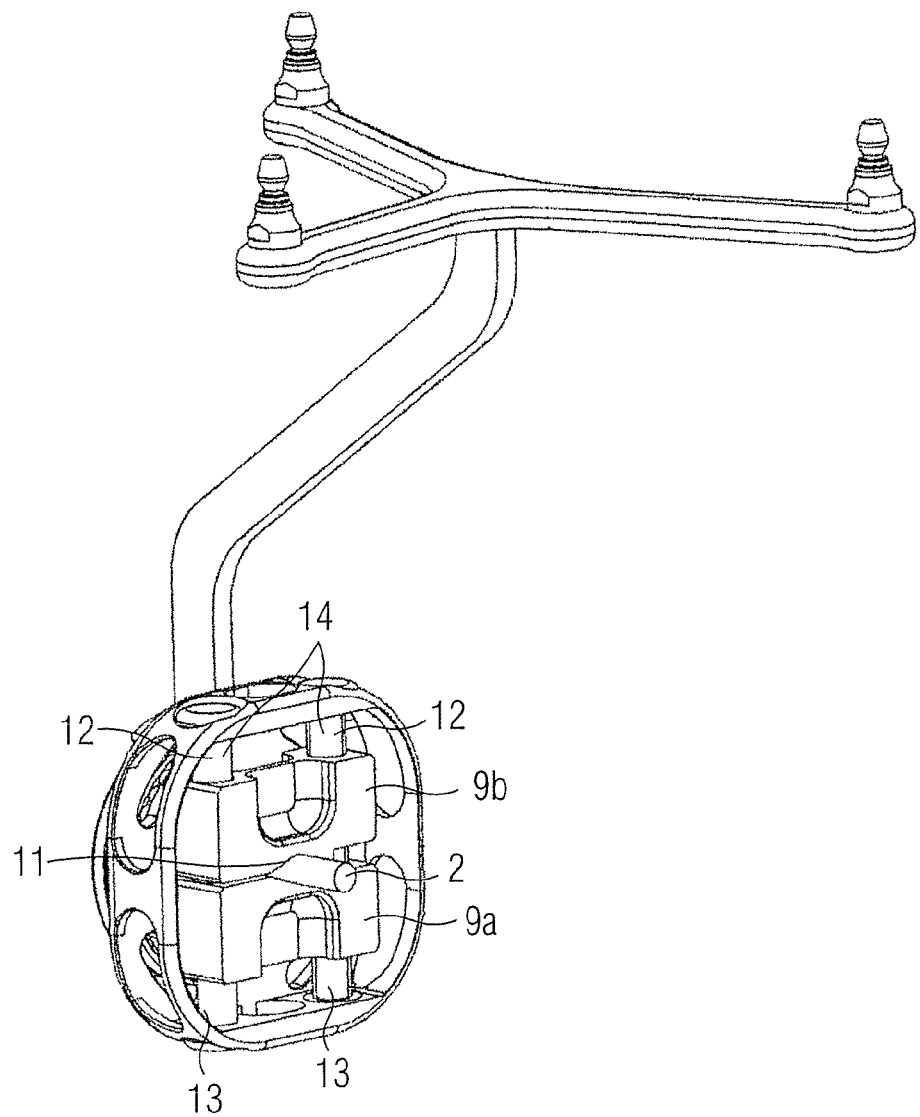
FIG. 5 is a rear view of the mount from FIG. 4.

FIGS. 4 and 5 show a second embodiment of a mount 1 according to the invention, wherein the same reference characters are used for the same components. Here as well a support 8 is provided on the back side of which are provided two clamp jaws 9a, 9b that in turn have corresponding clamp surfaces 11 that attack an instrument 2 to be clamped. As with regard to the described embodiment, the support 8 is executed somewhat in the manner of a housing, meaning that the clamp jaws 9a, b can essentially be arranged inside it, opening to the rear.

Here the two clamp jaws 9a, 9b are not directed linearly on separate linear guides, which is different than in the embodiment described above. For linear guidance—but also for clamp jaw movement for the purpose of clamping the instrument 2—two bolts 12 are provided with two threaded segments 13, 14 rotating opposite one another, wherein the respective threaded segments 13 engage at one clamp jaw and the respective threaded segments 14 engage at the other clamp jaw. Here as well, both bolts can be rotated either with a screwdriver or purely manually in order to clamp the instrument 2.

As in the embodiment described in the preceding, an annular segment 15 is also provided on the support. An annular segment 15 is provided on the rotation bearing 16 in the form of a roller bearing 17, and in this embodiment—as in the embodiment described in the preceding—a slide bearing can also be used instead of a roller bearing 17. The inner ring of the rotation bearing 16 is again arranged in a fixed manner on the annular segment 15, and therefore on the support 8, while the arm 19 of the localization device 3 is again arranged via a corresponding attachment segment 20 on the outer ring 18. This means that in this embodiment as well the support 8—together with the clamped instrument 2—can be rotated relative to the arm 19 or, respectively, the localization device 3.

Although as described above the operating physician manually rotates the instrument—thus the drill or the like, for example—and consequently engages with his or her other hand at the arm 19 (which consequently retains the localization device 3), it is also possible to use the method according to the invention in connection with a device for automatic instrument positioning and instrument movement. For example, such a device is a robot arm at which a device to rotate the instrument is arranged. For example, for this the instrument is initially to be affixed to the robot, after which the mount is attached to the instrument via the clamp jaws 9a, 9b. For example, the arm 19 can be coupled with the robot arm and a suitable bracket, such that in this embodiment as well the localization device 3 is fixed so that it does not move unintentionally.

The mount according to the invention is consequently universally usable and allows coupling with different instruments. Moreover, a position detection that is ensured at any point in time is also possible since there is always a visual or signal contact between the localization device 3 and the localization system 5. Furthermore, the mount has a very simple design and application. Due to its use in a critical environment, a thorough cleaning or disinfection is possible without any additional measures due to the open design of the mount, because the steam serving for steam sterilization or the disinfection agent (disinfectant) can wash around every component of the mount.

Although modifications and changes may be suggested by those skilled in the art, it is the intention of the inventor to embody within the patent warranted hereon all changes and modifications as reasonably and properly come within the scope of his contribution to the art.

We claim as our invention:

1. A mount to accommodate an oblong medical instrument, having a longitudinal instrument axis, for computer-assisted surgery, said mount comprising:
    a clamp bracket having an adjustable interior cross-section configured to clamp and thereby fix the oblong medical instrument in said clamp bracket, with the longitudinal instrument axis proceeding through said clamp bracket perpendicularly to said cross-section;
    a bearing comprising an inner bearing ring fixedly attached to said clamp bracket, and an outer bearing ring, said clamp bracket, and the oblong medical instrument fixed in said clamp bracket, being rotatable around said longitudinal axis together with said inner bearing ring, relative to said outer bearing ring;
    a localization structure configured to provide position information allowing detection and determination of a spatial position of the localization structure; and
    a support element rigidly attaching said localization structure to said outer bearing and thereby giving said localization structure a fixed spatial relation to said medical instrument fixed in said clamp bracket, and thereby, via said position information also allowing detection and determination of a spatial position of the medical instrument fixed in said clamp bracket due to said fixed spatial relation of said localization structure thereto.

2. A mount as claimed in claim 1 wherein said bearing is selected from the group consisting of roller bearings and slide bearings.

3. A mount as claimed in claim 1 wherein said clamp bracket comprises two clamp jaws that are moveable relative to each other to clamp said oblong medical instrument therebetween, and at least one adjustment element that controls movement of said two clamp jaws to selectively clamp and release said oblong medical instrument with respect to said clamp bracket.

4. A mount as claimed in claim 3 wherein said two clamp jaws are mounted in said clamp bracket so as to be linearly movable relative to each another.

5. A mount as claimed in claim 4 comprising a linear guide in which said two clamp jaws are retained and supported.

6. A mount as claimed in claim 4 wherein said clamp bracket comprises two adjustment elements that respectively individually control movement of said two clamp jaws.

7. A mount as claimed in claim 3 wherein said at least one adjustment element comprises a bolt having two threaded segments, said two threaded segments being respectively oppositely threaded and respectively engaging said two clamp jaws to cause said two clamp jaws to move toward and away from each other upon rotation of said bolt.

8. A mount as claimed in claim 1 wherein said localization structure comprises at least one localization element thereon that is adapted to be detected by an external detection device to produce said position information.

9. A mount as claimed in claim 8 wherein said at least one localization element is selected from the group consisting of optical markers and electromagnetic coils.

\* \* \* \* \*